United States Patent [19]
Engman

[11] Patent Number: 5,137,508
[45] Date of Patent: Aug. 11, 1992

[54] DISPOSABLE PROTECTIVE BANDAGE FOR ANIMALS

[76] Inventor: Paul Engman, 803 Amiford Dr., San Diego, Calif. 92107

[21] Appl. No.: 627,347

[22] Filed: Dec. 14, 1990

[51] Int. Cl.$^5$ ..................... A61F 13/00; A61F 15/00
[52] U.S. Cl. ..................... 602/79; 602/61; 2/22; 2/24; 119/143
[58] Field of Search ............... 128/157, 165, 166, 169, 128/171; 2/22, 24, 44, 256, 258; 119/143; 54/79; 606/201, 203

[56] References Cited

U.S. PATENT DOCUMENTS

| | | | |
|---|---|---|---|
| 2,717,437 | 9/1955 | De Mestral | 2/235 |
| 3,141,443 | 7/1964 | Huey | 119/143 |
| 3,276,041 | 10/1966 | Jonas | 2/258 |
| 3,738,330 | 6/1973 | Alofsin | 119/143 |
| 3,895,628 | 7/1975 | Adair | 128/171 |
| 4,355,600 | 10/1982 | Zielinski | 128/159 |
| 4,385,592 | 5/1983 | Goldstein | 119/143 |
| 4,489,676 | 12/1984 | Colquist | 119/143 |

*Primary Examiner*—David Isabella
*Assistant Examiner*—Paul Prebilic
*Attorney, Agent, or Firm*—Frank D. Gilliam

[57] ABSTRACT

A disposable protective bandage for protecting an animal's abdominal or leg surgical incisions or sutures or injuries from licking or scratching. An elongated, strong, chew-resistant, elasticized fabric mesh sheet is adapted to be wrapped around the torso or a leg of an animal after injury or surgery. The sheet is sufficiently elastic to closely and snugly conform to the shape of the animal's body to be protected. The ends of the sheet are secured together, preferably by a hook-and-loop fastening means. Where the torso is wrapped, the fastener should be at the top of the back where it cannot be easily chewed or scratched. When wrapped around a leg, excess material can be trimmed away, providing a smooth surface difficult to chew or scratch. A plurality of soft plastic stays are secured to the sheet, transverse to the length of the sheet. Two or more rows of stays may be provided where a leg is wrapped to provide for joint flexing. A pocket may be provided intermediate the sheet ends for a gauze pad or the like. The sheet and stays flex with the animals movement and provide support, making the animal more comfortable and protecting the wound or incision against licking, infection, scratching or other injury.

22 Claims, 1 Drawing Sheet

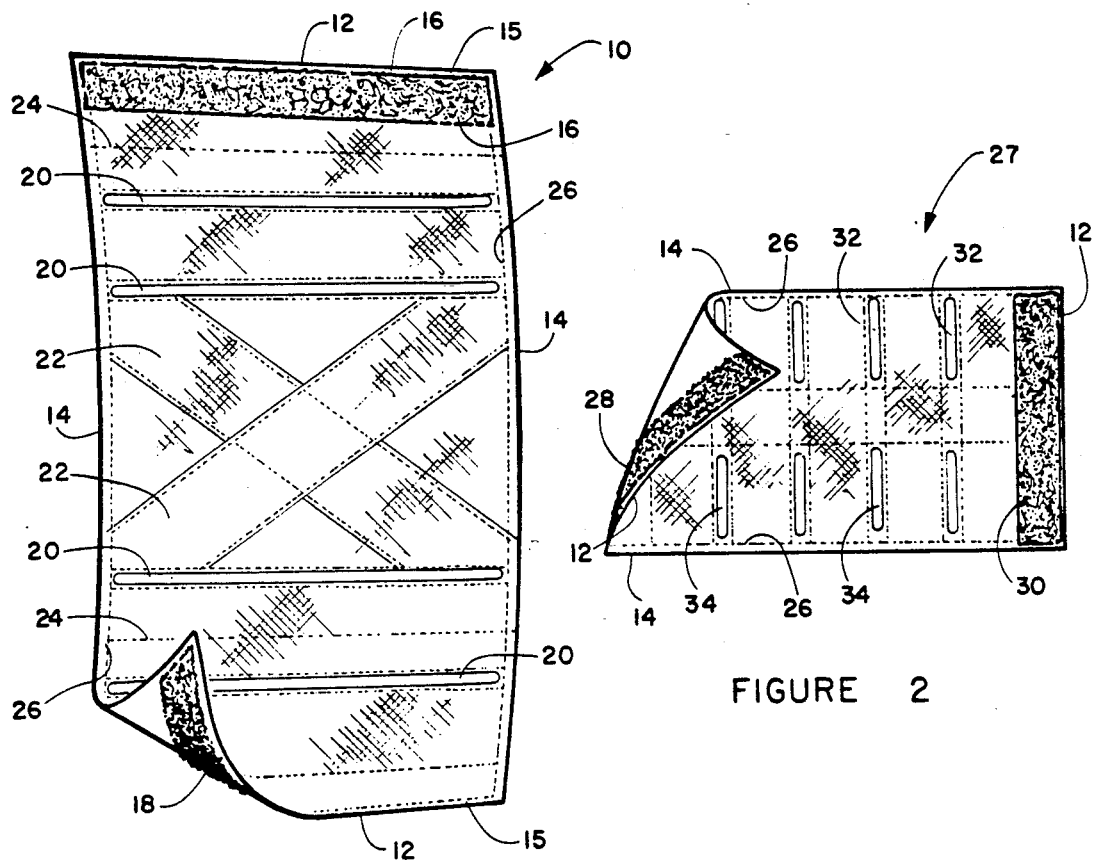
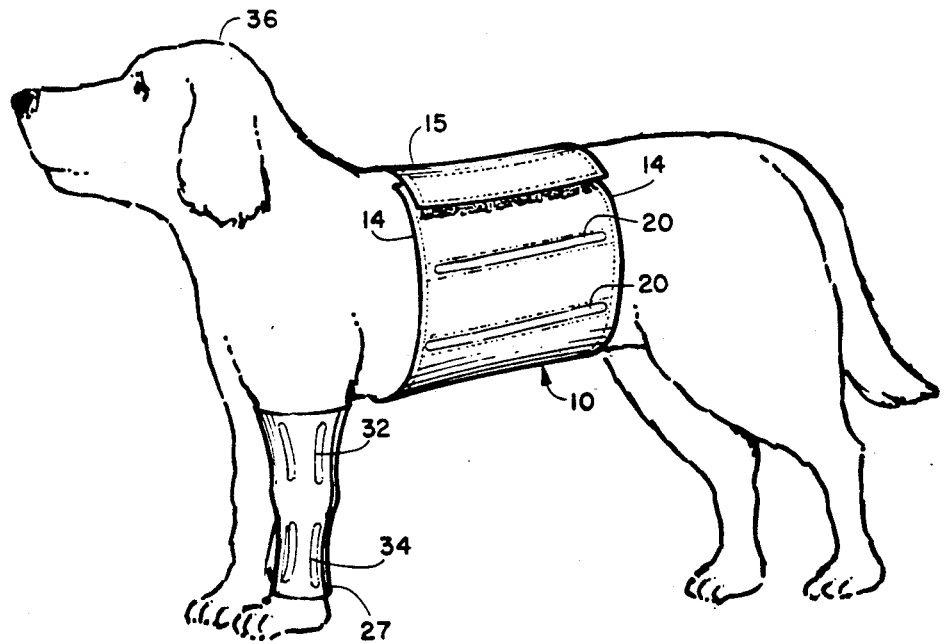
FIGURE 1
FIGURE 2
FIGURE 3

DISPOSABLE PROTECTIVE BANDAGE FOR ANIMALS

BACKGROUND OF THE INVENTION

This invention relates in general to bandages and, more specifically, to a disposable protective support bandage for animals.

A number of different sweaters, protective covers, bandages, braces and other protective devices have been developed for a variety of purposes. In general these have not been effective because of the propensity of an animal, such as a dog or cat, to chew or scratch the cover or bandage, eventually damaging or removing the cover and often aggravating a wound or incision being protected.

Typical of these are the body suits or covers described by Zielinski in U.S. Pat. No. 4,355,600 and Huey in U.S. Pat. No. 3,141,443. These suits cover the entire torso of the animal, with openings for head and legs. The tend to be hot and uncomfortable. Since the suits do not fit animals of different sizes well, there are loose edges and attachments which can be chewed or scratched to the point that the protective portion of the suit is dislodged.

Other bandages are relatively narrow and surround a portion of the animal's torso. Typical of these are the bandages or protective devices described by Alofsin in U.S. Pat. No. 3,738,330 and Adair in U.S. Pat. No. 3,895,628. These bands either require complex hardnesses to secure them to the animal's body or simply include narrow bands around the animal's torso. In either case, the bandage is easily dislodged by scratching or licking. Also, the soft, cloth-like bandages tend to bunch-up and become narrow as the dog moves, greatly reducing the protection provided.

Other protective devices include a number of straps and braces to hold the device in place. Typical of these are the devices disclosed by Goldstein in U.S. Pat. No. 4,385,592 and Colquist in U.S. Pat. No. 4,489,676. While adequate for very specialized purposes, such as immobilizing the neck after neck surgery or the like, these devices are very complex and easily susceptible to shifting or damage through chewing or scratching. These devices are expensive and not suitable for disposal after a single use, thus posing the danger of transferring infections or diseases to later users.

Thus there is a continuing need for improved protective bandages for animals.

SUMMARY OF THE INVENTION

It is, therefore, an object of this invention to provide a disposable protective bandage for animals which overcomes the above-noted problems. Another object is to provide a support bandage that breaths through its surface to promote healing. Yet another object of this invention is to provide a disposable protective bandage which is resistant to being dislodged by scratching or chewing. A further object is to provide a bandage giving superior support and resistance to bunching or narrowing. Yet another object is to provide a bandage of improved simplicity and ease of use.

The above objects, and others, are accomplished in accordance with this invention, basically, by a bandage for animal torsos or legs which comprises a sheet of elastic fabric mesh having a first pair of opposite edges adapted to be wrapped around a selected portion of an animal's body and secured together to hold the bandage in place. The first edges may be approximately parallel or may be angled slightly to accommodate shapes such as a dog's torso which is not precisely round and of a uniform diameter. Generally the second edges are approximately parallel, with some divergence near the second ends in some cases. The bandages may, or course, be tailored to fit animals of different sizes and dimensions. The sheet material is selected so as to be sufficiently elastic to permit tight, snug, support to the wrapped portion.

Typically, said first edges are held together by hook-and-loop panels, hooks and eyes, snaps or the like. Where the torso is wrapped, the bandage will preferably be installed with the closure at the top of the back, limiting access for scratching or chewing. If the bandage is wrapped around a leg,, a hook-and-loop fastener, such as that available under the VELCRO trademark, should be used, with excess fastener cut away after installation to eliminate any loose end that the animal might be able to reach with its teeth.

A plurality of spaced soft plastic stays are provided to prevent bunching of the bandage in use and improve body support. Preferably, at least a majority of the stays are approximately parallel to said first edges and to each other. Where the bandage is to be place across a joint in a leg, two approximately parallel rows of stays are preferred with a gap at the joint to permit comfortable flexing of the joint.

A pocket may be provided in the bandage intermediate said first edges to receive a gauze pad or the like over a would or incision. Doublers or diagonal added layers of the elastic fabric may be provided over the bandage to increase strength or reduce stretch in selected directions and in selected areas.

The bandage of this invention is primarily intended for dogs, cats and other small animals. In some cases, such as very small children, unconscious or semi-conscious adult humans, persons suffering from senility or the like, the capability of this bandage to support a body portion and resist manual damage to a wound or incision being protected and resist undirected, unconscious or unintended, efforts to move or remove the bandage could be very valuable.

BRIEF DESCRIPTION OF THE DRAWING

Details of the invention, and of preferred embodiments thereof, will be further understood upon reference to the drawing, wherein:

FIG. 1 is a plan view of a bandage prior to use;

FIG. 2 is a plan view of a second embodiment of the bandage; and

FIG. 3 is an elevation view of the bandage of FIG. 1 in place on a dog's torso and the bandage of FIG. 2 in place on a dog's legs.

DETAILED DESCRIPTION OF PREFERRED EMBODIMENTS

Referring now to FIG. 1, there is seen a plan view of a typical bandage 10 according to this invention. Bandage 10 includes first edges 12 and second edges 14. Bandage 10 is made from any suitable elastic material. Preferably, the material has an open mesh, is substantially equally elastic in all directions and is moisture and tear resistant. Preferred materials include nylon, polyethylene, polypropylene, or the like and combinations thereof.

Fasteners 15 are arranged along first edges 12. Any suitable fastening means may be used. Typical fasteners include snaps, hooks and eyes and hook-and-loop material. Of these, hook-and-loop material, typically available under the VECLCRO trademark, is preferred because of its tenacity when brought together, easy of removal when pulled vertically away from the overlapped area and the ease of varying the degree of overlap and, thus, the circumference of the bandage. Also, this material will allow the bandage ends to be overlapped and secured at an angle where the torso has an unusual shape. A hook area 16 and a loop area 18 are schematically located in FIG. 1. The conventional loop matt would be on the opposite side and not seen in FIG. 1.

A plurality of thin, soft but longitudinally stiff, stays 20 are sewn into pockets across the central portion of bandage 10. While the stays 20 may be used in any suitable orientation, best results are generally obtained where they are substantially parallel to each and substantially perpendicular to second edges 14. While stays 20 may be formed from any suitable material, in general a plastic strip material is preferred for the optimum combination of stiffness and flexibility. If desired, localized reinforcing material such as the "X" pattern of strips indicated schematically by broken lines 22 may be provided.

In some cases it will be desired to provide a sheet of material against the inner surface of the bandage (not seen in FIG. 1), sewn to the bandage along lines schematically indicated at 24 and along one edge 14 to form a pocket for receiving a gauze sheet, pad or the like.

FIG. 2 shows an alternate embodiment particularly suitable for use on an animals limb, positioned across a joint. Bandage 27 has first edges 12 and second edges 14. Areas carrying fastening means, such as a hook-and-loop means with a hook area at 28 and a loop area on the reverse side of area 30 are provided along first edges 12, as described above.

In this embodiment, two spaced rows of soft but stiff stays 32 and 34 are provided, with a flexible space therebetween. While each row of stays may be oriented in any suitable manner, for best results they generally should lie in two substantially parallel rows, with the stays in each row substantially parallel to each other and substantially perpendicular to second edges 14.

An edge reinforcement 26 or material 7 cross stitching may be provided to increase edge resistance to chewing or scratching.

A typical use of the bandages of FIGS. 1 and 2 is shown in FIG. 3. The bandage 10 of FIG. 1 is shown wrapped and fastened around the torso of dog while bandages according to the FIG. 2 embodiment are shown around a front and back leg.

As can be seen, the fastener 15 is positioned at the top of the dog's back where the dog cannot easily reach it to bite or scratch the fastener. Stays 20 prevent bunching and of the bandage when the dog moves which could cause edges 14 to move together, severely reducing bandage effectiveness. Thus, a comfortable, difficult to disrupt bandage is provided for such cases as spaying, other abdominal surgery or injury in those areas.

Bandages 27 of FIG. 2 are shown wrapped around a front and a rear leg of dog 36. The wrapping is as described above, except the space between stay rows 32 and 34 is positioned over the leg joint so that dog 27 can easily run and walk with minimal discomfort. The stays prevent bunching up or narrowing of the bandage. In this embodiment, the hook-and-loop material is particularly preferred, since after applying the bandage snugly to the leg, any excess end material can be easily cut away, leaving a smooth wrap which is resistant to removal or damage by chewing or scratching.

While certain preferred materials, conditions and arrangements were described in detail in the above description of preferred embodiments, those may be varied, where suitable, with similar results. For example, medicated pads may be placed within the bandages or in pockets in the bandage, and the bandages may be provided with localized sewn-on reinforcements as desired. Other variations, ramifications and applications of this invention will occur to those skilled in the art upon reading this disclosure. Those are intended to be included within the scope of this invention, as defined in the appended claims.

I claim:

1. A disposable protective support bandage which comprises:

a generally rectangular elastic fabric sheet;

said sheet having a first and second pair of opposite edges;

fastening means extending along said first pair of opposite edges for releasably fastening the first pair of opposite edges of said sheet together therealong to form a generally enclosed tubular configuration of a selected circumference; and a plurality of flexible stays secured to said sheet substantially perpendicular to the second opposite edges of said sheet.

2. The bandage according to claim 1 wherein said sheet is sized to wrap around a torso of an animal, said animal having, a region along the back and front and back legs with said torso therebetween, said cover enclosing more than half the distance between said front and back legs with said fastening means meeting in said region along the back of the animal.

3. The bandage according to claim 1 wherein said fastening means comprises wide, overlapping bands of hook-and-loop material whereby the circumference of said tubular configuration is widely variable.

4. The bandage according to claim 1 further including a pocket intermediate the first opposite edges of said sheet adapted to receive a pad.

5. The bandage according to claim 1 wherein said fastening means comprises hook-and-eye fasteners and said sheet is sufficiently elastic to adapt to a range of circumferences.

6. The bandage according to claim 1 wherein said fastening means comprises cooperating snaps and said sheet is sufficiently elastic to adapt to a range of circumferences.

7. The bandage according to claim 1 wherein said stays are arranged in a single row of substantially parallel stays along the central portion of said sheet.

8. The bandages according to claim 1 wherein said stays are arranged in at least two rows of parallel stays along the central portion of said sheet, the stays of each row being substantially parallel with the stays of each other row whereby said sheet can flex intermediate said rows of stays.

9. The bandage according to claim 1 wherein said stays are formed from flexible plastic materials.

10. The bandage according to claim 1 wherein said sheet is formed from an elastic open-mesh material selected from the group consisting of nylon, polyethylene, polypropylene, and combinations thereof.

11. The bandage according to claim 1 wherein an additional layer of said fabric is secured to a selected area of said sheet as a localized reinforcement.

12. The bandage according to claim 1 further including an area of reinforcing cross-stitching along said second opposite edges.

13. A disposable protective support bandage which comprises:
   a generally rectangular elastic fabric sheet;
   said sheet having a first and second pairs of opposite edges;
   hook-and-loop fastening material covering areas adjacent to said first opposite edges of said sheet for releasably fastening the first pair of opposite edges of said sheet together to form a generally tubular configuration of selected circumference; and
   a substantially parallel array of elongated flexible stays secured to said sheet substantially perpendicular to the second opposite edges of said sheet.

14. The bandage according to claim 13 further including a pocket intermediate the first opposite edges of said sheet adapted to receive a pad.

15. The bandage according to claim 13 wherein said stays are arranged in a single row of substantially parallel stays along the central portion of said sheet.

16. The bandage according to claim 15 wherein said sheet is sized to wrap around a torso of an animal having a back region and front and back legs with said torso therebetween and covers more than half the distance between said front and back legs with said fastening means meeting in said back region of the animal.

17. The bandages according to claim 13 wherein said stays are arranged in at least two rows of parallel stays along the central portion of said sheet, the stays of each row being substantially parallel with the stays of each other row whereby said sheet can flex intermediate said rows of stays.

18. The bandage according to claim 17 wherein said sheet is sized to wrap around a leg of an animal, said leg having a leg joint with the space between the rows of stays aligned with said leg joint.

19. The bandage according to claim 13 wherein said stays are formed from flexible plastic materials.

20. The bandage according to claim 13 wherein said sheet is formed from an elastic open-mesh material selected from the group consisting of nylon, polyethylene, polypropylene and combinations thereof.

21. The bandage according to claim 13 wherein an additional layer of said fabric is secured to a selected area of said sheet as a localized reinforcement.

22. The bandage according to claim 13 further including an area of reinforcing cross-stitching along said second opposite edges.

* * * * *